(12) United States Patent
Salvati

(10) Patent No.: US 6,359,644 B1
(45) Date of Patent: Mar. 19, 2002

(54) MEASUREMENT SYSTEM FOR VIDEO COLPOSCOPE

(75) Inventor: Jon R. Salvati, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 09/144,936

(22) Filed: Sep. 1, 1998

(51) Int. Cl.⁷ .................................................. H04N 7/18
(52) U.S. Cl. ............................ 348/65; 348/68; 348/77
(58) Field of Search ........................... 348/77, 141, 66, 348/65, 68

(56) References Cited

U.S. PATENT DOCUMENTS

| | | | |
|---|---|---|---|
| 3,730,632 A | | 5/1973 | Chikama |
| 4,115,804 A | | 9/1978 | Morton et al. |
| 4,917,488 A | | 4/1990 | Glass |
| 4,980,763 A | | 12/1990 | Lia |
| 5,070,401 A | * | 12/1991 | Salvati et al. .................. 348/77 |
| 5,552,822 A | | 9/1996 | Nallakrishnan |
| 5,577,130 A | | 11/1996 | Wu |
| 5,867,217 A | * | 2/1999 | Okino et al. .................. 348/358 |
| 6,088,612 A | * | 7/2000 | Blair .......................... 600/407 |
| 6,101,408 A | * | 8/2000 | Craine et al. ................ 600/425 |

* cited by examiner

Primary Examiner—Andy Rao
(74) Attorney, Agent, or Firm—Wall Marjama & Bilinski LLP

(57) ABSTRACT

There is a remote visual inspection device measurement system comprising a lens system having selected optical characteristics and a CCD imager. The system includes a video display and an image overlay generator to select the target object in the video display. The image overlay generator allows the operator to mark the image and determines the number of pixels between cursor marks. The system includes a focusing mechanism including a focus motor with a servo feedback that provides focus data and a zoom mechanism including a zoom motor with a servo feedback that provides zoom data. The system includes a microprocessor/CPU that calculates the size of the target object by mathematically manipulating the optical characteristics, the focus data, the zoom data, and the pixel data.

21 Claims, 5 Drawing Sheets

MEASUREMENT SYSTEM FOR VIDEO COLPOSCOPE

This invention relates generally to video inspection systems, and more specifically relates to a measurement system in a video inspection system.

BACKGROUND OF THE INVENTION

There are numerous situations that arise while using a video inspection system, particularly a remote video inspection system, where there is a need to determine the size of a target object that appears within the video field. In the medical arena for example, when a doctor utilizes a video colposcope to inspect the vagina, cervix and/or uterus of a patient, it is important to be able to determine the size of certain objects within the video field. For instance, if a lesion/pathology appears in the video field, it is important to quantify the size of the object to determine the extent of the lesion/pathology and to determine if treatments are effective in reducing the lesion/pathology.

To date, determining the size of an object that appears in the video field has been accomplished through various means. One such method is described in U.S. Pat. No. 5,577,130 to Wu. Wu discloses a method and apparatus for determining the distance between an image and an object. The invention employs stereo vision methodology for determining depth information between an object and an image. The method involves displacing the imaging means (camera) and utilizes at least two of the successive images of an object that are generated. The relationship between the amount of displacement and the disparity in pixels in the successive images is used to mathematically determine the distance of an object from the video imaging means.

Another method is described in U.S. Pat. No. 5,070,401 to Salvati et al., which patent is owned by a common assignee of the present applicant. Salvati discloses a method of video measurement with automatic calibration and distortion correction. The method involves projecting a known supplementary image into the target area, counting the pixels associated with the known supplementary image, calibrating the system by using the known information, counting the pixels associated with the object of interest in the targets, and determining the physical characteristics of the object of interest.

Another method of determining the size of an object in a video field is described in U.S. Pat. No. 4,980,763 to Lia, which patent is owned by a common assignee of the present applicant. Lia discloses a system for measuring the size of objects viewed with a borescope. The patent discloses the use of a shadow generating means and image detecting means to detect the image of the object of interest and the contrasting shadow. The size of the object of interest can be calculated by measuring parameters of the contrasting image.

Yet another method is described in U.S. Pat. No. 4,115,804 to Morton et al. Morton discloses a method of image analysis for identifying measurement data from single and multiple fields of scan and for the control of feature measurement generation through the use of keyboard and visual displays. The invention is intended to overcome the effects of noise variability in obtaining alignment between points between different fields of scan and successful correlation of information obtained from successive fields of scan.

Another method is described in U.S. Pat. No. 3,730,632 to Chikama. Chikama discloses an object measurement system for an endoscope. The system projects an image of the target onto an image viewing surface. The image viewing surface comprises a scale indicating the length measurement. The scale is proportionately varied in relation to relative movement of an object lens assembly, said movement serving to focus the image of the object on the viewing surface.

The prior art contains methods of measurement that require at least two successive images in order to determine the measurement, which entails complex mathematical calculations and requires increased computer memory. The prior art also contains methods that an image of a supplementary object which is either integral to or projected into the video field. There is a need to provide a simpler apparatus and method of calculating the size of an object that appears in a video image. There is also the need to provide an apparatus and method of calculating the size of an object that appears in a video image that does not require relatively complex mathematical manipulations or the need for supplementary images within the video field.

OBJECTS AND SUMMARY OF THE INVENTION

It is therefore an object of the invention to provide an improved means of measuring an object through a video inspection system.

It is another object of the invention to provide an improved means of measuring an object through a video inspection system without the need to use successive images to determine the measurement.

It is yet another object of the invention to provide an improved means of measuring an object through a video inspection system without the need to provide a supplemental image within the video field.

These and other objects are accomplished by providing a measurement system comprising a lens system having selected optical characteristics and a CCD imager. The system includes a video display and an image overlay generator to select the target object in the video display. The image overlay generator allows the operator to mark the image and determines the number of pixels between cursor marks. The system includes a focusing mechanism including a focus motor with a servo feedback that provides focus data and a zoom mechanism including a zoom motor with a servo feedback that provides zoom data. The system includes a microprocessor/CPU that calculates the size of the target object by mathematically manipulating the optical characteristics, the focus data, the zoom data, and the pixel data.

BRIEF DESCRIPTION OF THE DRAWINGS

For a fuller understanding of the nature and objects of the invention, reference should be made to the following detailed description of a preferred mode of practicing the invention, read in connection with the accompanying drawings, in which.

DETAILED DESCRIPTION OF THE INVENTION

Figure 1:
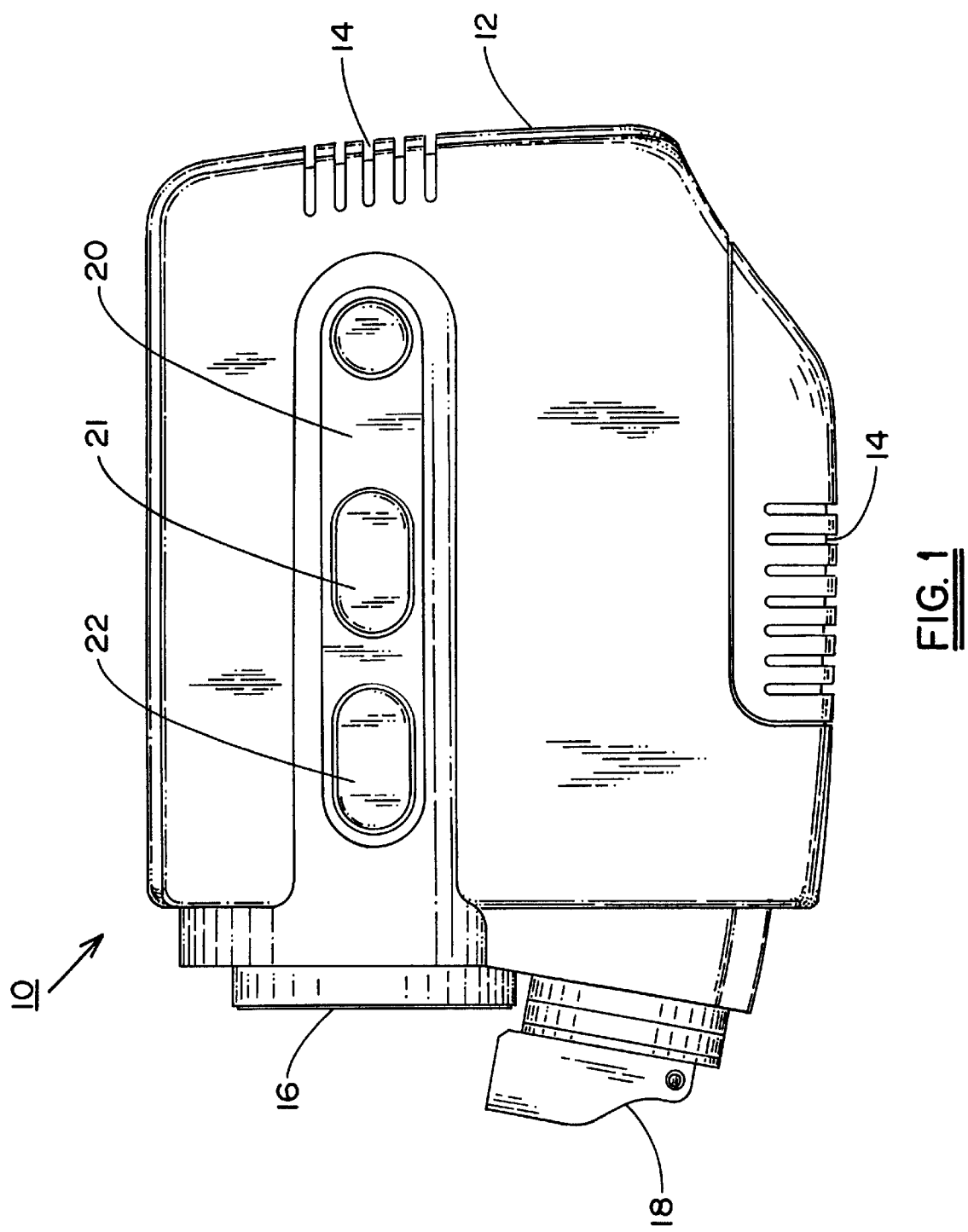
FIG. 1 is a side plan view of a video colposcope.
Figure 2:
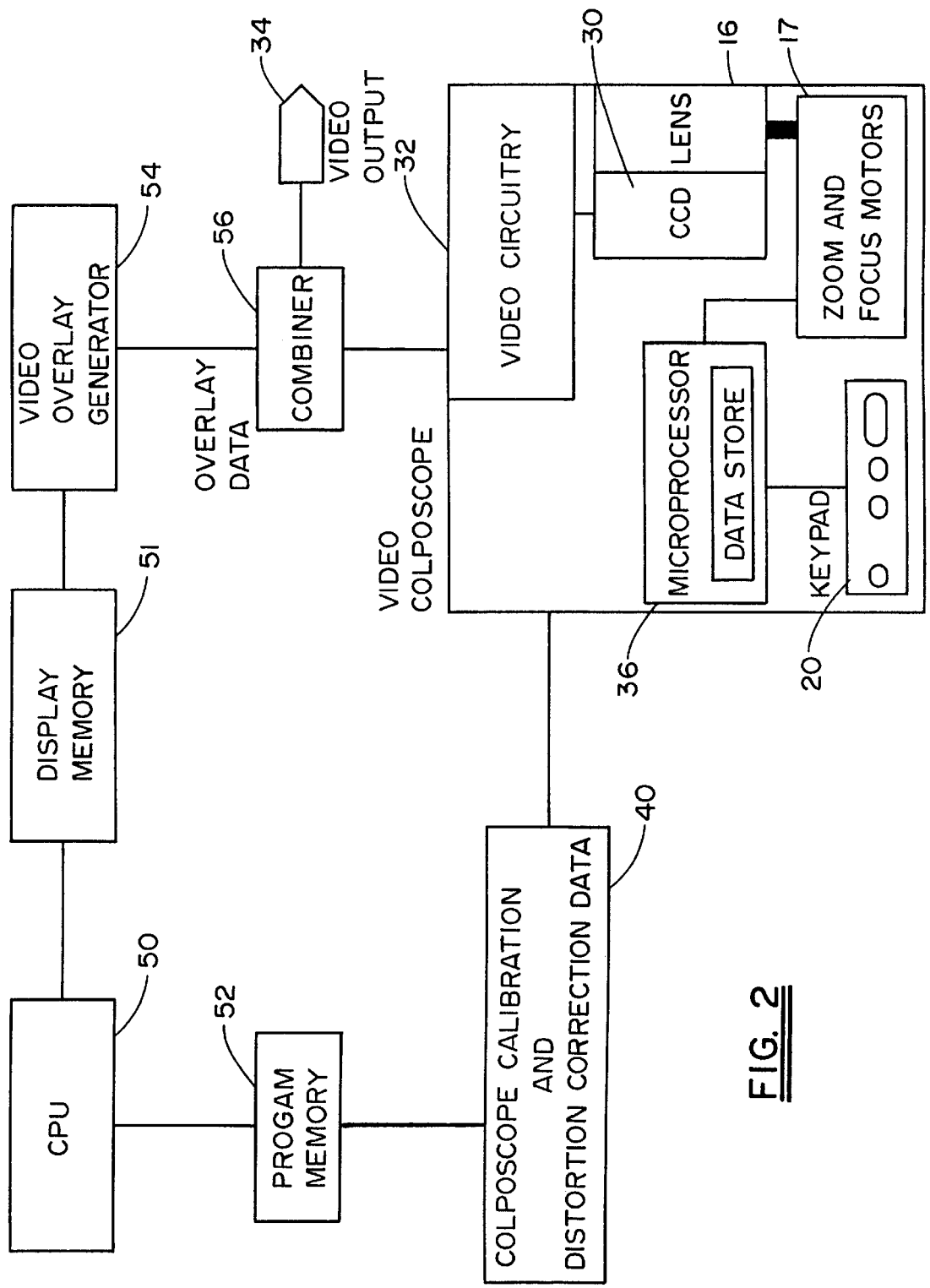
FIG. 2 is a block diagram of the video colposcope.

Referring now to FIG. 1, there is shown a video colposcope 10, which presently is the preferred mode of practicing the invention. One skilled in the art recognizes that there are numerous potential applications in the area of remote visual inspection and that the description of the invention herein is the best mode now known by the applicant and is not meant to limit the application of the invention to the field of colposcopy. The colposcope 10 includes a housing 12. The housing 12 is constructed of a high impact plastic and preferably contains venting areas 14 for heat dissipation. The colposcope includes a lens or lens system 16 which projects an image of a selected target onto a video image pick-up, preferably a charge coupled device 30, commonly referred to as a CCD (see FIG. 2). As is well known in the art, the CCD 30 electronically captures an image of the video field in a digital format and the digital information is relayed to video circuitry 32. The video circuitry 32 relays the information to a video output 34 such as a display screen or data collection/transmission device (not shown). The colposcope 10 also includes an adjustable illumination beam director 18 which provides illumination to the video field.

The lens system 16 has inherent optical characteristics such as distortion, focal length, and field of view, some of which are used in the calculation of the target size as is described in detail below. The preferred lens characteristics of the colposcopic system include a focal length of 300 mm, a field of view 66 mm–14 mm, and a depth of field of 112 mm–5 mm. The zoom capability of the preferred embodiment is 4.5×–25×. The aforementioned lens characteristics are the preferred mode for a video colposcope and one skilled in the art would recognize that the characteristics of the lens would differ depending upon the selected video inspection system. The lens system 16 is comprised of a series of lenses that interact to change the focus and zoom. As is known in the art, the system includes motors 17 (FIG. 2) that manipulate the positioning of the various individual lenses in relation to each other and in relation to the CCD in order to effect different foci and zoom configurations. The video colposcope 10 includes an integral keypad 20 with a zoom control pad 21 and a focus control pad 22 which the operator uses to send signals to the focus and zoom motors 17 in order to change the positioning of the lenses for optimum viewing. The focus and zoom motors 17 contain servo-feedback mechanisms which provide information to a microprocessor 36, and eventually the data is used by the central processing unit (CPU) 50 of the system in the calculation of the size of the target object, as is explained in detail below.

Figure 3:
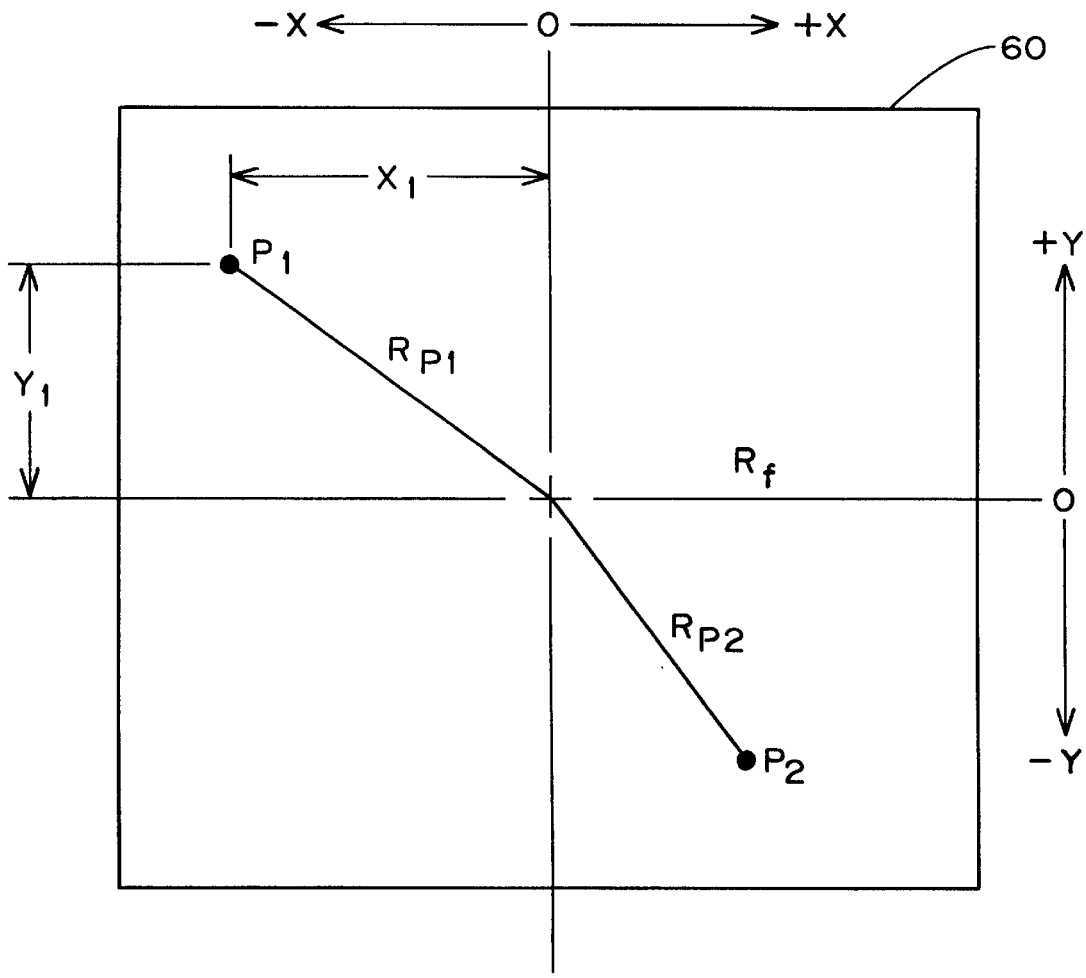
FIG. 3 is a front view of a video screen with a graphical overlay.
Figure 4:
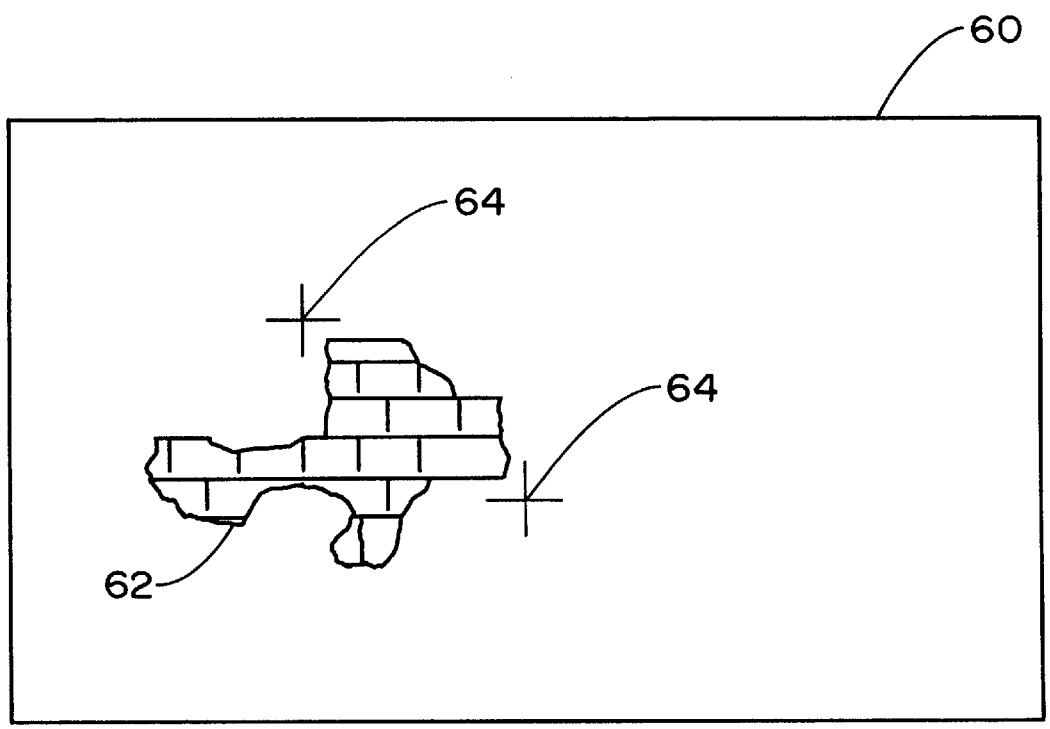
FIG. 4 is a front view of a video screen.
Figure 5:
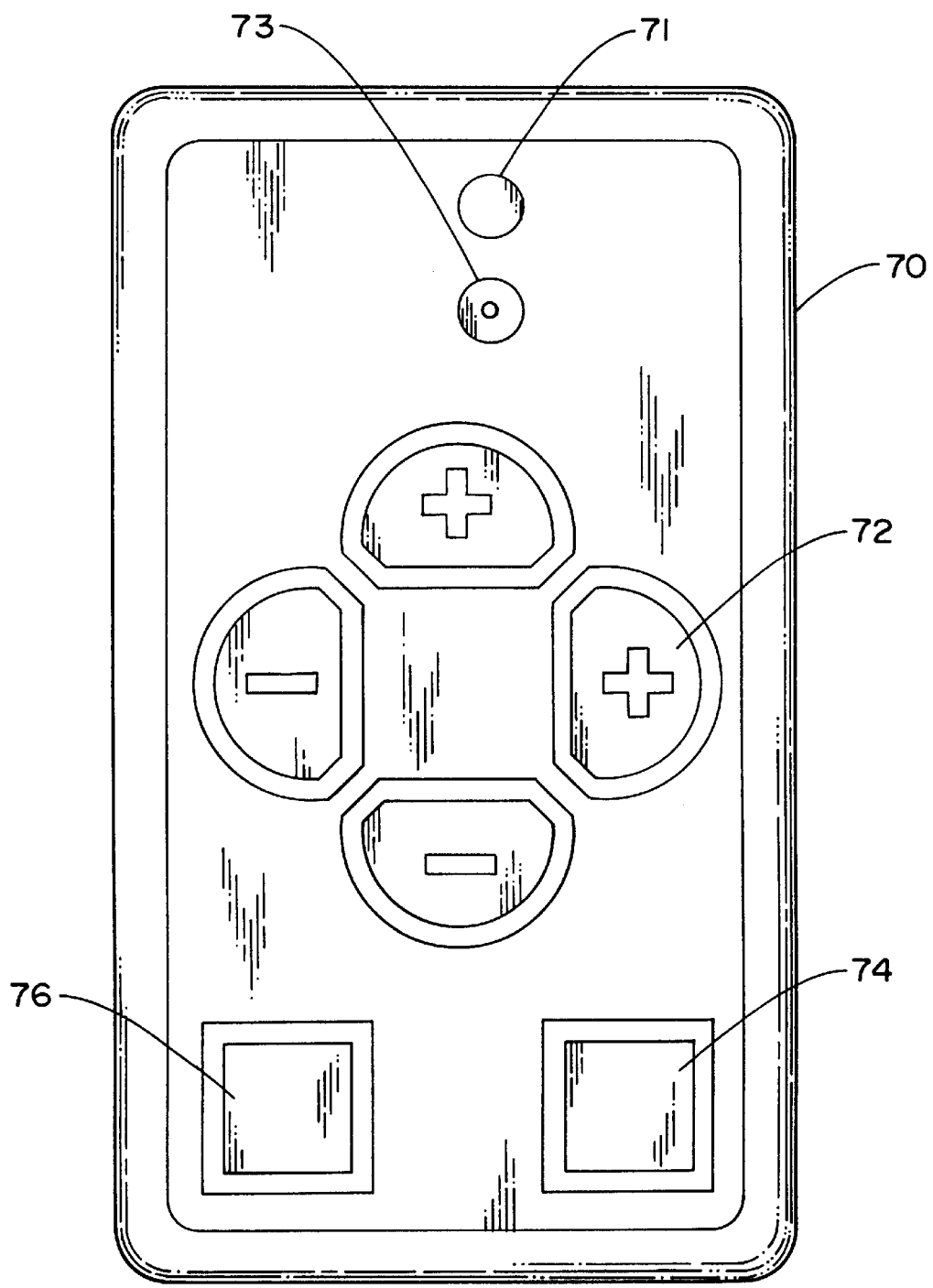
FIG. 5 is a front view of a keypad.

Referring now to FIG. 4, there is a video display screen 60 which displays the video field, including the target object 62 which is to be measured. As is known in the art, the video display screen 60, or video monitor, is comprised of number of pixels. The system includes a video overlay generator 54 (FIG. 3), which generates an information display which overlays the video image. The information display includes measurement cursors 64—64 which are manipulated by the user and are used to mark the target object 62 to be measured, as depicted in FIG. 4. Referring now to FIG. 5, the measurement cursers 64 are controlled by the operator and in the preferred embodiment the operator uses a keypad 70 to control the movements of the cursors. Of course, other means to move and mark the cursor positions are known to those skilled in the art, such as a computer mouse. The keypad 70 can be integral to the colposcope 10 or can be connected by an umbilical (not shown). The keypad 70 includes four cursor positioning keys 72 that move the cursors on the screen in the horizontal and vertical planes. The keypad 70 includes a cursor marking key 74 which, when depressed by the operator, marks the position of the cursor 64 on the screen at one end of the target object 62. The operator then moves the cursor 64 to another point on the screen at the other end of the target object 62. When the second point on the screen has been reached, the cursor marking key 74 is again depressed, and that point is also marked on the screen. In this manner, the operator places marks at the periphery of the target object 62 as it appears on the screen 60. The distance in pixels between the marks is used in the calculation of the size of the target object 62, as explained below in more detail.

In order to determine the size of an object, the first step is to determine the optical distortion correction of a point of the lens system at a given magnification, and preferably for ease of calculation the magnification at M=1× is determined. Referring now to FIG. 3, there is depicted a screen 60 made up of a number of pixels with a graphical representation overlaid to show how the optical distortion correction of a point is used to determine the distance between two points. For simplicity of explanation, the pixels that are depicted have a ratio of 1:1, as opposed to the standard NTSC ratio of 4:3. One skilled in the art would recognize the appropriate mathematical manipulation required to convert between the ratios. The lens system has a known distortion fraction at the flat of square. The optical distortion correction of a point $C_{p1}$ is determined by the formula:

$$Cp_1 = \frac{1}{1 + D_1} = \frac{1}{1 + \frac{(D(R_{p_1}))^2}{R_f^2}}$$

$$Cp_1 = \frac{1}{\frac{1 + (D((X_1^2 + Y_1^2)^{.5}))^2}{R_f^2}}$$

where
Rf=Radius to Flat
Rp=Radius to Point
$D_1$=Distortion fraction at Point
D=Distortion fraction at flat of square
$CP_1$=Correction factor for distortion unmapping of $P_1$.

After the optical distortion correction factor is determined for a point, the value of the coordinates any two particular points can be determined by:

$X_{1_c}$=Distortion Corrected=$Cp_1X_1$
$Y_{1_c}$=Distortion Corrected=$Cp_1Y_1$
$X_{2_c}$=Distortion Corrected=$Cp_1X_2$
$Y_{2_c}$=Distortion Corrected=$Cp_1Y_2$ Knowing the distortion corrected values, the distance Pn between points $P_1(X_1,Y_1)$ and $P_2(X_2Y_2)$ is determined by:

$$Pn=((X_{1_c}-X_{2_c})^2+(Y_{1_c}-Y_{2_c})^2)^{.5}$$

Knowing the value of Pn at magnification M=1, the size of a target object on the video screen after the operator has brought the object into view and focused is determined by:

Object Size=M*K*Pn
Where K is a constant

The constant K is determined by using the known characteristics of the lens. The constant K will vary depending upon the type of lens and imager used, but once the characteristics are determined for a particular lens and imager, the number is a constant The constant K may also contains the conversion math for the measurement system, i.e. inches, centimeter, or millimeters. The calculation of K is determined using the following formula:

$$K = \frac{1}{(\text{\# of pixels}) * L}$$

where L is determined by:

$$L = \frac{\left(\frac{1}{(1-V)}\right)}{2 * OD * \text{TAN}\left(\frac{FOV}{2}\right)}$$

where
- V=the percent distortion across horizontal axis of lens
- OD=Object Distance
- FOV=Field of View (across an axis, preferably the horizontal axis)

In use, the video colposcope 10 is positioned to provide an adequate view of the target area 62. The video colposcope 10 is automatically calibrated 40 when powered up, which includes the distortion correction data and also includes the focus and magnification motors being zeroed. The target object 62 is brought into the preferred viewing configuration on the screen 60 by the operator using the focus 21 and zoom buttons 22. The exact object distance (OD) is determined by feedback from the focus motor and calculating the deviation from zero. The magnification factor M is determined by the position of the zoom and focus motor servo-feedbacks 17 and is stored in data storage/microprocessor 36. The CCD 30 relays the video information to the video circuitry 32, which then relays the video information to the video output 34 via a combiner 56. The video display information is also stored in display memory 51. The video overlay generator 54 is activated by the operator manipulating the keypad 70 (FIG. 5) by depressing the measurement key 71, which causes the generation of the on-screen cursor 64. The operator manipulates the cursor 64 to mark the periphery of the object 62 using the cursor keys 72 and the marking key 74. After the operator has marked the periphery of the object, the operator depresses the measuring key 76 which causes the overlay data from the combiner 56 to be forwarded to the CPU 50. The size of the object is determined using the calculation algorithms which are stored in program memory 52. The operator returns the colposcope to non-measurement mode by depressing the colposcope key 73.

An example of the calculation of the size (in inches) of a target object of 768 pixels as marked on the monitor using a lens having a 90 degree field of view with a 20% visual distortion across the horizontal axis of lens and an object distance of 2.0 inches is:

Assuming M=2 and Pn=100 pixels $$L = \frac{\left(\frac{1}{(1-.2)}\right)}{2 * (2.0 \text{ inch}) * \text{TAN}\left(\frac{90}{2}\right)}$$

$$L = \frac{(1.25)}{2 * (2) * \text{TAN}(45°)}$$

$$L = \frac{(1.25)}{4 * 1} = .3125/\text{inch}$$

$$K = \frac{1}{(768 \text{ pixels} * .3125/\text{inch})}$$

Object Size = $M * K * Pn$
= $2 \times (0.0042 \text{ inch/pixel}) \times 100 \text{ pixels}$
= $0.84$ inches Of course, in addition to the linear size of an object, the area of an object can be also be calculated. For example, the area of a generally square shaped object could be determined by marking the four corners of the object, determining the distance between the four corners using the method discussed above, and then applying the appropriate geometrical formula.

While the present invention has been particularly shown and described with reference to the preferred mode as illustrated in the drawing, it will be understood by one skilled in the art that various changes in detail may be effected therein without departing from the spirit and scope of the invention as defined by the claims.

I claim:

1. An apparatus for determining the size of a target object viewed with a video imager, said apparatus comprising:
    a lens system having selected optical characteristics;
    an imaging means for detecting an image, said image including the target object;
    a video display means to display said image;
    an image overlay means for selecting the target object in said image in said video display means, said image overlay means providing pixel data;
    a focusing means, said focusing means having a focus motor, said focus motor having a servo feedback, said focus motor servo feedback providing focus data;
    a zoom means, said zoom means having a zoom motor, said zoom motor having a servo feedback, said zoom motor servo feedback providing magnification data; and,
    calculating means for calculating the size of the target object, whereby the size of the target object is calculated by mathematically manipulating said optical characteristics, said focus data, said magnification data, and said pixel data.

2. The apparatus of claim 1 wherein said imaging means comprises a charge coupled device.

3. The apparatus of claim 1 wherein said video display means comprises a video monitor.

4. The apparatus of claim 1 wherein said image overlay means includes cursor means to mark the target object in said video display means.

5. The apparatus of claim 1 wherein said pixel data is optical distortion corrected.

6. The apparatus of claim 1 wherein said calculating means includes an algorithm to calculate the size of the target object, said algorithm including the steps of multiplying said pixel data by said magnification data by a constant (K).

7. The apparatus of claim 6 wherein said constant is dependent upon said optical characteristics, said optical characteristics including a first value (V) equal to the percent distortion across an axis of said lens, a second value (FOV) equal to field of view of said lens, and a third value (OD) equal to a distance from said lens to the object.

8. A method of determining the size of an object that appears in a video image generated using an electronic imaging system, said method comprising:
    providing a lens system having selected optical characteristics;

providing an imaging means for detecting an image, said image including the target object;

providing a video display means to display said image;

providing an image overlay means to select the target object in said image in said video display means, said image overlay means providing pixel data;

providing a focus means, said focus means having a focus motor, said focus motor having a servo feedback, said focus motor servo feedback providing focus data;

providing a zoom means, said zoom means having a zoom motor, said zoom motor having a servo feedback, said zoom servo feedback providing magnification data;

calculating the size of the object by mathematically manipulating said optical characteristics, said focus data, said magnification data, and said pixel data.

9. The method of claim 8 wherein said imaging means comprises a charge coupled device.

10. The method of claim 8 wherein said video display means comprises a video monitor.

11. The method of claim 8 wherein said image overlay means includes cursor means to mark the target object in said video display means.

12. The method of claim 8 wherein said pixel data is optical distortion corrected.

13. The method of claim 8 wherein said calculating means includes an algorithm to calculate the size of the target object by multiplying said pixel data by said magnification data by a constant.

14. The method of claim 13 wherein said constant is dependent upon said optical characteristics, said optical characteristics including a first value (V) equal to the percent distortion across an axis of said lens, a second value (FOV) equal to field of view of said lens, and a third value (OD) equal to a distance from said lens to the object.

15. A video colposcope, said colposcope comprising:

a lens system having selected optical characteristics;

an imaging means for detecting an image, said image including a target object;

a video display means to display said image;

an image overlay means for selecting said target object in said image in said video display means, said image overlay means providing pixel data;

a focusing means, said focusing means having a focus motor, said focus motor having a servo feedback, said focus motor servo feedback providing focus data;

a zoom means, said zoom means having a zoom motor, said zoom motor having a servo feedback, said zoom motor servo feedback providing magnification data; and, calculating means for calculating the size of said target object, whereby the size of said target object is calculated by mathematically manipulating said optical characteristics, said focus data, said magnification data, and said pixel data.

16. The colposcope of claim 15 wherein said imaging means comprises a charge coupled device.

17. The colposcope of claim 15 wherein said video display means comprises a video monitor.

18. The colposcope of claim 15 wherein said image overlay means includes cursor means to mark the target object in said video display means.

19. The colposcope of claim 15 wherein said pixel data is optical distortion corrected.

20. The colposcope of claim 15 wherein said calculating means includes an algorithm to calculate the size of said target object, said algorithm including the steps of multiplying said pixel data by said magnification data by a constant (K).

21. The colposcope of claim 20 wherein said constant is dependent upon said optical characteristics, said optical characteristics including a first value (V) equal to the percent distortion across an axis of said lens, a second value (FOV) equal to field of view of said lens, and a third value (OD) equal to a distance from said lens to the object.

* * * * *